(12) United States Patent
Ojha (10) Patent No.: US 11,701,278 B2
(45) Date of Patent: Jul. 18, 2023

(54) TECHNOLOGIES FOR EFFICIENTLY TRACKING THE LOCATION OF A PATIENT BED

(71) Applicant: Hill-Rom Services, Inc., Batesville, IN (US)

(72) Inventor: Unnati Ojha, Cary, NC (US)

(73) Assignee: Hill-Rom Services. Inc., Batesville, IN (US)

( * ) Notice: Subject to any disclaimer, the term of this patent is extended or adjusted under 35 U.S.C. 154(b) by 376 days.

(21) Appl. No.: 16/992,802

(22) Filed: Aug. 13, 2020

(65) Prior Publication Data

US 2021/0052450 A1    Feb. 25, 2021

Related U.S. Application Data

(60) Provisional application No. 62/890,736, filed on Aug. 23, 2019.

(51) Int. Cl.
*A61G 7/05*      (2006.01)
*G16H 40/20*    (2018.01)

(52) U.S. Cl.
CPC .............. *A61G 7/05* (2013.01); *G16H 40/20* (2018.01); *A61G 2203/12* (2013.01); *A61G 2203/20* (2013.01); *A61G 2205/60* (2013.01)

(58) Field of Classification Search
CPC .. A61G 7/05; A61G 2203/12; A61G 2203/20; A61G 2205/60
See application file for complete search history.

(56) References Cited

U.S. PATENT DOCUMENTS

| | | |
|---|---|---|
| 4,882,566 A | 11/1989 | Koerber, Sr. et al. |
| 7,868,740 B2 | 1/2011 | McNeely et al. |
| 8,125,318 B2 | 2/2012 | Heinbrock et al. |
| 8,169,304 B2 | 5/2012 | Schuman, Sr. et al. |
| 8,272,892 B2 | 9/2012 | McNeely et al. |
| 8,319,633 B2 | 11/2012 | Becker et al. |
| 8,334,777 B2 | 12/2012 | Wilson et al. |
| 8,384,526 B2 | 2/2013 | Schuman, Sr. et al. |
| 8,392,747 B2 | 3/2013 | Ferguson et al. |
| 8,461,968 B2 | 6/2013 | Ball et al. |
| 8,756,056 B2 | 6/2014 | Grill et al. |
| 9,711,029 B2 | 7/2017 | Ribble et al. |
| 9,999,375 B2 | 6/2018 | Hayes et al. |
| 10,716,474 B2 | 7/2020 | Bodurka et al. |

(Continued)

FOREIGN PATENT DOCUMENTS

| | | |
|---|---|---|
| EP | 1623666 A2 | 2/2006 |
| WO | WO 2008/098346 A1 | 8/2008 |

*Primary Examiner* — Fredrick C Conley
(74) *Attorney, Agent, or Firm* — Barnes & Thornburg LLP (57) ABSTRACT

A patient bed may include a tag reader that may be connected to antennas on opposite sides of the patient bed. The patient bed may also include circuitry configured to produce, with the tag reader and the antennas, an interrogation signal from the opposite sides of the patient bed, to cause a location tag that may be mounted to a doorway of a room to produce a response signal. The circuitry may also be configured to receive, with the tag reader and with one of the antennas, the response signal from the location tag. Additionally, the circuitry may be configured to determine, as a function of room data in the response signal, a present location of the patient bed.

17 Claims, 5 Drawing Sheets

(56) References Cited

U.S. PATENT DOCUMENTS

| | | |
|---|---|---|
| 2007/0150554 A1 | 6/2007 | Simister |
| 2007/0210917 A1 | 9/2007 | Collins, Jr. et al. |
| 2010/0079304 A1* | 4/2010 | Becker .................. A61B 5/1113 |
| | | 340/286.07 |
| 2013/0048705 A1 | 2/2013 | Tallent et al. |
| 2013/0091631 A1 | 4/2013 | Hayes et al. |
| 2014/0297327 A1 | 10/2014 | Heil et al. |
| 2015/0033295 A1 | 1/2015 | Huster |
| 2015/0081335 A1 | 3/2015 | Dixon et al. |
| 2015/0128346 A1 | 5/2015 | Hollyoak et al. |
| 2015/0231006 A1 | 8/2015 | Bhimavarapu et al. |
| 2016/0038361 A1 | 2/2016 | Bhimavarapu et al. |
| 2016/0296143 A1* | 10/2016 | Hayes .................. A61B 5/0022 |
| 2018/0296415 A1 | 10/2018 | Seim |
| 2019/0150737 A1 | 5/2019 | Bodurka et al. |

* cited by examiner

TECHNOLOGIES FOR EFFICIENTLY TRACKING THE LOCATION OF A PATIENT BED

CROSS-REFERENCE TO RELATED APPLICATION

This application claims the benefit, under 35 U.S.C. § 119(e), of U.S. Provisional Patent Application No. 62/890,736, filed Aug. 23, 2019, the entirety of each of which is hereby expressly incorporated by reference herein.

BACKGROUND

The present disclosure relates to tracking the locations of medical equipment in a building and particularly, to using wireless communication to track the locations of patient beds.

Tracking the locations of medical equipment, such as patient beds, in a hospital or other building is important in efficiently providing care to patients (e.g., knowing which room a caregiver should visit in order to assist a particular patient). Some systems may rely on barcodes affixed to walls of patient rooms that, when scanned, provide identifying data about the room (e.g., the room number) which may then be entered into a tracking system in association with a particular piece of medical equipment (e.g., a patient bed) and a patient (e.g., a patient supported by the bed). However, a drawback of such systems is that the barcodes may become unreadable over time, due to fading, scratching, and general wear and tear.

Other systems rely on manual entry (e.g., by a caregiver) of medical equipment locations. However, such systems may be prone to user error (e.g., entering the wrong room number by mistake) and are labor intensive. Yet other systems rely on complex installations of tracking devices (e.g., infrared tracking devices) throughout the building to continually monitor the locations of medical equipment. However, typically, each of the devices in the system requires a dedicated power source, invasive installation operations, a significant upfront cost to purchase the collection of tracking devices, and significant ongoing expenses to repair and replace the devices as they wear out.

SUMMARY

The present application discloses one or more of the features recited in the appended claims and/or the following features which, alone or in any combination, may comprise patentable subject matter:

According to an aspect of the present disclosure, a patient bed may include a tag reader that may be connected to antennas on opposite sides of the patient bed. The patient bed may also include circuitry that may be configured to produce, with the tag reader and the antennas, an interrogation signal from the opposite sides of the patient bed, to cause a location tag that may be mounted to a doorway of a room to produce a response signal. The circuitry may also be configured to receive, with the tag reader and with one of the antennas, the response signal from the location tag. Additionally, the circuitry may be configured to determine, as a function of room data in the response signal, a present location of the patient bed.

In some embodiments, the tag reader may produce the interrogation signal as a radio frequency signal having a linear polarization. In some embodiments, in determining, as a function of the room data, the present location of the patient bed, the circuitry may determine, from the room data, an identifier of the room. The circuitry may determine, from a number of detections of the room identifier, whether the patient bed has entered or exited the room. Further, in doing so, the circuitry may determine, from a number of detections of the room identifier separated by a predefined time period (e.g., 10 seconds), whether the patient bed has entered or exited the room. For example, the circuitry may identify separate detections of the room identifier alternatingly as entrances into or exits from the room.

In some embodiments, the circuitry in the patient bed may determine the location of the patient bed as a function of whether the patient bed has been connected to a power source within a predefined time period (e.g., five minutes) of receipt of the response signal from the location tag. For example, the circuitry may determine, in response to a determination that the patient bed has been connected to a power source within the predefined time period, that the patient bed entered the room. Conversely, the circuitry may determine, in response to a determination that the patient bed has not been connected to a power source within the predefined time period, that the patient bed exited the room.

In some embodiments, the circuitry in the patient bed may determine, as a function of the room data, whether the room has multiple patient bed sublocations. Further, the circuitry may produce, in response to a determination that the room has multiple sublocations, a prompt on a user interface of the patient bed, to designate one of the sublocations as the present location of the patient bed. The circuitry may then receive, with the user interface, the designation (e.g., from a caregiver) of one of the sublocations as the present location of the patient bed. In some embodiments, the circuitry may send, to a remote computer device, data indicative of the present location of the patient bed. Additionally or alternatively, the circuitry may display, on a graphical user interface, data indicative of the present location of the patient bed.

In another aspect of the present disclosure, a method may include producing, with a tag reader that may be connected to antennas on opposite sides of a patient bed, an interrogation signal from the opposite sides of the patient bed. The interrogation signal may cause a location tag mounted to a doorway of a room to produce a response signal. The method may also include receiving, with the tag reader and with one of the antennas, the response signal from the location tag. Additionally, the method may include determining, by the patient bed and as a function of room data in the response signal, a present location of the patient bed.

In some embodiments, producing the interrogation signal may include producing a radio frequency signal having a linear polarization. Additionally or alternatively, determining, as a function of the room data, a present location of the patient bed may include determining, from the room data, an identifier of the room. In some embodiments, determining, as a function of the room data, the present location of the patient bed may include determining, from a number of detections of the room identifier by the patient bed, whether the patient bed has entered or exited the room. For example, the method may include identifying separate detections of the room identifier alternatingly as entrances into or exits from the room. In some embodiments, the method may include determining the location of the patient bed further as function of whether the patient bed has been connected to a power source within a predefined time period (e.g., five minutes) of receipt of the response signal.

In another aspect of the present disclosure, a system may include a location tag that may be mounted to a doorway of a room. The location tag may be a passive radio frequency identification tag configured to use energy in an interrogation signal to send a response signal that contains room data. Additionally, the system may include a medical device that includes a tag reader that may be connected to antennas on opposite sides of the medical device. The medical device may also include circuitry configured to produce, with the tag reader and the antennas, the interrogation signal from the opposite sides of the medical device, to cause the location tag that may be mounted to the doorway of a room to produce the response signal. Additionally, the circuitry may be configured to receive, with the tag reader and with one of the antennas, the response signal from the location tag. Further, the circuitry may be configured to determine, as a function of the room data in the response signal, a present location of the medical device.

In another aspect, one or more computer-readable storage media may comprise a plurality of instructions that, when executed, cause circuitry in a patient bed to produce, with a tag reader that may be connected to antennas on opposite sides of the patient bed, an interrogation signal from the opposite sides of the patient bed, to cause a location tag mounted to a doorway of a room to produce a response signal. The instructions may also cause the circuitry to receive, with the tag reader and with one of the antennas, the response signal from the location tag. Additionally, the instructions may cause the circuitry to determine, as a function of room data in the response signal, a present location of the patient bed.

Additional features, which alone or in combination with any other feature(s), such as those listed above and/or those listed in the claims, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures in which.

DETAILED DESCRIPTION

While the concepts of the present disclosure are susceptible to various modifications and alternative forms, specific embodiments thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. Additionally, it should be appreciated that items included in a list in the form of "at least one of A, B, and C" can mean (A); (B); (C); (A and B); (A and C); (B and C); or (A, B, and C). Similarly, items listed in the form of "at least one of A, B, or C" can mean (A); (B); (C); (A and B); (A and C); (B and C); or (A, B, and C).

The disclosed embodiments may be implemented, in some cases, in hardware, firmware, software, or any combination thereof. The disclosed embodiments may also be implemented as instructions carried by or stored on a transitory or non-transitory machine-readable (e.g., computer-readable) storage medium, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

Figure 1:
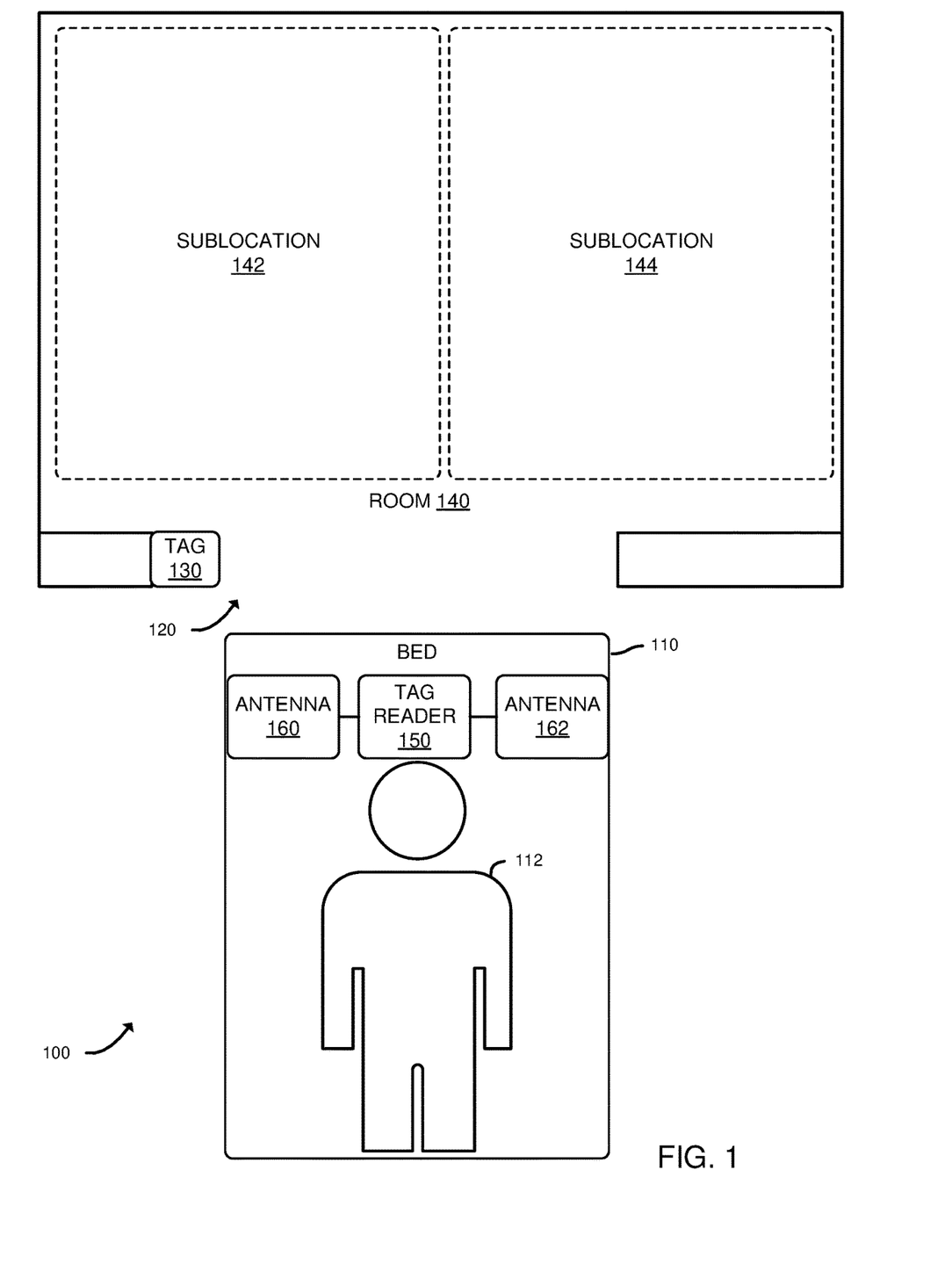
FIG. 1 is a simplified diagram of at least one embodiment of a system for efficiently tracking the location of medical equipment.

Referring now to FIG. 1, a system 100 for efficiently tracking the location of medical equipment includes a patient bed (also referred to herein as a "bed") 110 supporting a patient 112, and a room 140 in which the bed 110 may be temporarily located. In the illustrative embodiment, a location tag 130 is mounted to a doorway 120 (e.g., a door frame, an entrance, etc.) of the room. In the illustrative embodiment, the tag 130 is mounted in range between the highest available position and the lowest available position of the bed 110. The location tag 130 may be embodied as any device or circuitry (e.g., a passive radio frequency identification (RFID) tag, a near field communication (NFC) tag, etc.) configured to use energy provided by an interrogation signal (e.g., a radio frequency signal) and to send a response signal (e.g., a radio frequency signal) that includes room data (e.g., an identifier of the room, such as a room number, identifiers of sublocations 142, 144 in the room where the bed 110 can be placed, etc.) encoded in the location tag 130.

The bed 110 is equipped with a tag reader 150 connected to multiple antennas 160, 162. The tag reader 150 may be embodied as any device or circuitry (e.g., an RFID reader) configured to periodically produce an interrogation signal that, if received by a location tag (e.g., the location tag 130), causes the location tag to produce the response signal. The tag reader 150 is further configured to receive the response signal and use circuitry to identify (e.g., parse) data, such as the room data, within the response signal. In the illustrative embodiment, the antennas 160, 162 are located on opposite sides of the bed 110 to enable the interrogation signal to reach the location tag 130 when the bed 110 is in the doorway 120, regardless of which side of the bed 110 the location tag is closest to (e.g., regardless of whether the bed 110 is entering the room 140 or leaving the room 140).

In some embodiments, reader 150 and antennas 160, 162 are mounted to a base frame of bed 110 and in other embodiments, reader 150 and antennas 160, 162 are mounted to an upper frame of bed 110. Beds having upper frames that are raisable, lowerable, and tiltable relative to base frames are well known in the art. Beds 110 are typically transported with the upper frames moved to a lowest position relative to the base frames. Thus, the elevational position relative to doorway 120 at which tag 130 should be positioned for successful wireless communication with antenna 160, 162 is generally known based on either the height of the antennas 160, 162 on the base frame or on the upper frame in its lowest position relative to the base frame.

In the illustrative embodiment, the antennas 160, 162 face sideways (e.g., towards the door frame, rather than up) and emit an interrogation signal that has a linear polarization (e.g., the electric field vector or magnetic field vector of the electromagnetic radiation is confined to a given plane along the direction of propagation), thereby providing greater range for a given amount of power consumption than if the interrogation signal had a circular polarization. This is not to say that antennas having circular polarization could not be used in other embodiments. Further, and as described in more detail herein, the system 100 uses only one location tag 130 per room, rather than multiple locations tags (e.g., one mounted to an interior surface of the doorway 120 and another tag mounted to an exterior surface of the doorway 120), to reduce equipment, installation, and maintenance costs as compared to systems that use multiple location tags per room. To compensate for the reduction in location tags per room, and as described in more detail herein, the bed 110 includes circuitry configured to execute operations that determine whether the bed 110 has entered or exited a given room after receiving a response signal from a location tag (e.g., the location tag 130).

Figure 2:
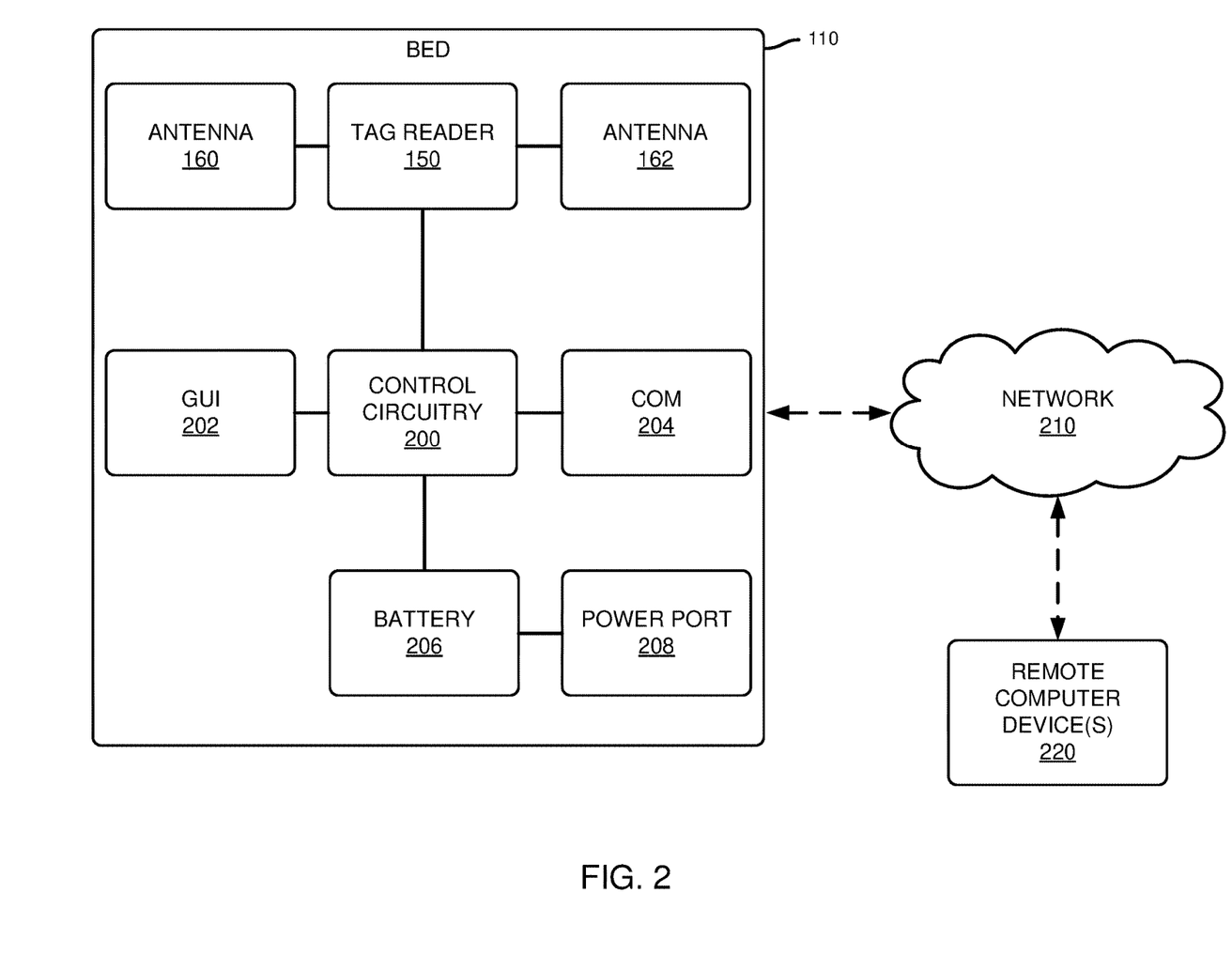
FIG. 2 is a block diagram of at least one embodiment of components of a patient bed included in the system of FIG. 1.

Referring now to FIG. 2, the bed 110, in the illustrative embodiment, includes the tag reader 150 and the antennas 160, 162, described above with reference to FIG. 1. Additionally, the bed 110 includes control circuitry 200 connected to the tag reader 150, a graphical user interface 202, communication circuitry 204, and a battery 206, which is connected to a power port 208. The control circuitry 200 may be embodied as any device or circuitry (e.g., a processor, a microcontroller, a field programmable gate array (FPGA), an application specific integrated circuit (ASIC), reconfigurable circuitry, etc.) and/or software configured to perform the location tracking operations described herein (e.g., causing the tag reader 150 to periodically send the interrogation signal, parsing data within a response signal received by the tag reader 150, determining the location of the bed 110 based at least in part on data in the response signal, sending data indicative of the present location of the bed 110 to a remote computer device 220, displaying the present location on the GUI 202, etc.).

The GUI 202 may be embodied as, or otherwise use, any suitable display technology including, for example, a liquid crystal display (LCD), a light emitting diode (LED) display, a cathode ray tube (CRT) display, a plasma display, and/or other display usable in a computer device. The display may include a touchscreen sensor that uses any suitable touchscreen input technology to detect a user's tactile selection of information displayed on the display including, but not limited to, resistive touchscreen sensors, capacitive touchscreen sensors, surface acoustic wave (SAW) touchscreen sensors, infrared touchscreen sensors, optical imaging touchscreen sensors, acoustic touchscreen sensors, and/or other type of touchscreen sensors. As described herein, the GUI 202 may be used to display the present location of the bed 110 and/or to display prompts to the user (e.g., a prompt to select a sublocation 142, 144 within the room 140) and to receive input from the user (e.g., a designation of which sublocation 142, 144 the bed 110 has been moved to). In the some embodiments, the GUI 202 is located on a siderail (not shown) of the bed 110.

The communication circuitry 204 may be embodied as any communication circuit, device, or collection thereof, capable of enabling communications over a network 210 between the bed 110 and another computer device (e.g., the remote computer device(s) 220, etc.). The communication circuitry 204 may be configured to use any one or more communication technology (e.g., wired or wireless communications) and associated protocols (e.g., Ethernet, Wi-Fi®, WiMAX, Bluetooth®, cellular, etc.) to effect such communication. In some embodiments, the communication circuitry 204 may include a cable connector, such as a 37-pin connector port.

The battery 206 may be embodied as any device or circuitry (e.g., one or more electrochemical cells with external connections) configured to power electrical devices within the bed 110 (e.g., the control circuitry 200 and devices connected thereto) and to be recharged from an external source (e.g., a wall outlet in the room 140) via the power port 208. The power port 208 may be embodied as any device or circuitry (e.g., transformer(s), capacitor(s), diode(s), and/or other power electronics) to provide electrical power from an external source to the battery 206 and/or other components of the bed 110. In doing so, the power port 208 may convert the power from AC (alternating current) to DC (direct current), adjust a voltage of power, and/or perform other operations to condition the power for use by the other components of the bed 110.

The remote computer device(s) 220 may be embodied as any computer device(s) capable of communicating with the bed 110 (e.g., through the network 210) to track the location of the bed 110 (e.g., based on location data sent by the bed 110) over time. For example, the remote computer device(s) 220 may operate an electronic medical records (EMR) system or a nurse call system that includes, among other data, the locations of medical equipment (e.g., the bed 110).

The network 210 may be embodied as any type of data communication network, including a global network (e.g., the internet), a one or more wide area network (WANs), local area networks (LANs) digital subscriber line (DSL) networks, cable networks (e.g., coaxial networks, fiber networks, etc.), cellular networks (e.g., Global System for Mobile Communications (GSM), 3G, Long Term Evolution (LTE), Worldwide Interoperability for Microwave Access (WiMAX), etc.), radio access networks (RANs), or any combination thereof.

Figure 3:
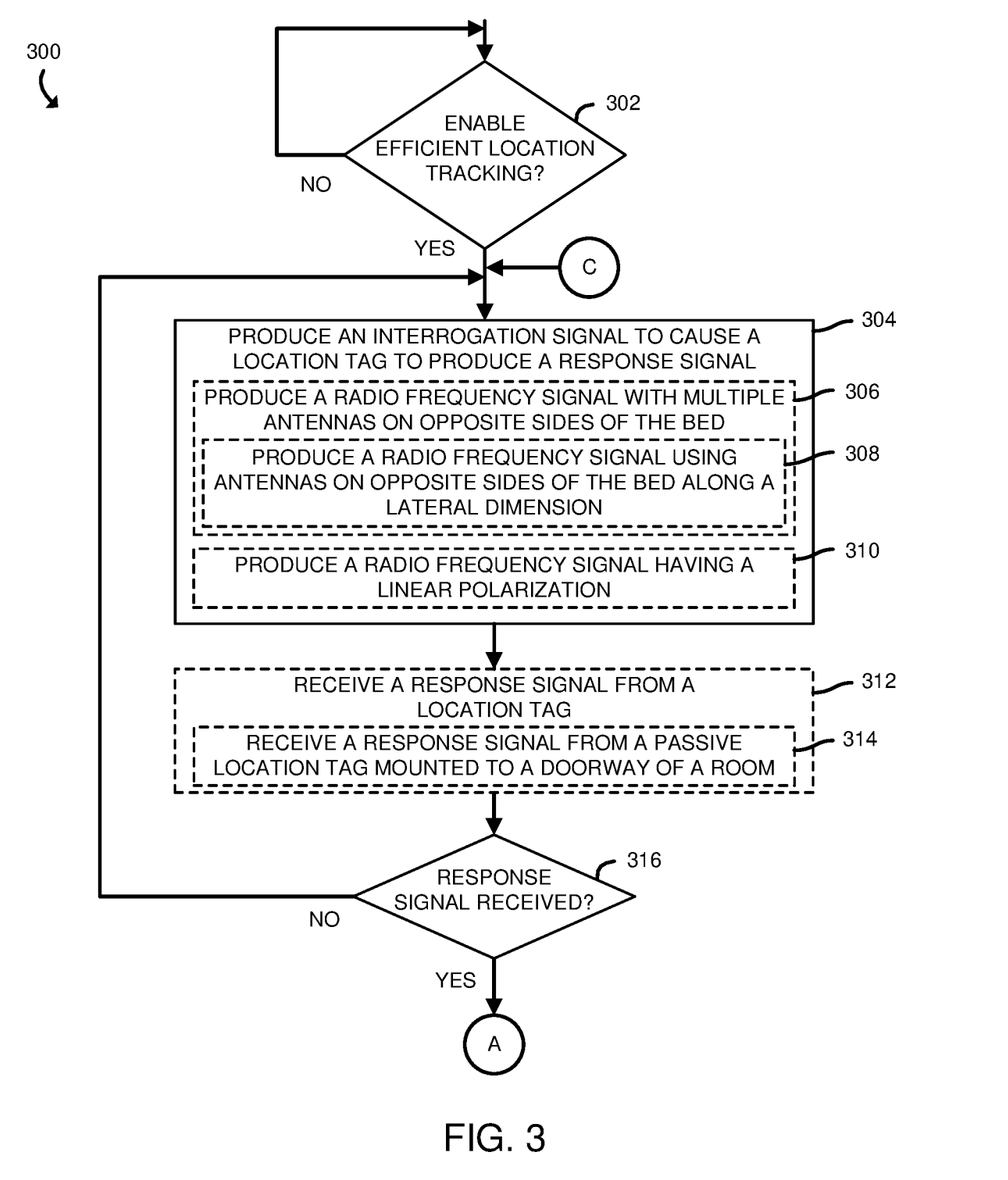
FIGS. 3-5 are simplified flow diagrams of at least one embodiment of a method for performing efficient location tracking that may be performed by the patient bed of FIGS. 1 and 2.

Referring now to FIG. 3, the bed 110, in operation, may perform a method 300 of efficient location tracking. In the illustrative embodiment, the method 300 begins with block 302 in which the bed 110 determines whether to enable efficient location tracking. In doing so, the bed 110 may determine whether the tag reader 150 and antennas 160, 162 are present, whether a configuration setting (e.g., in a memory of the control circuitry 200) indicates to enable efficient location tracking, whether a request has been received from another computer device (e.g., from the remote computer device(s) 220) to enable efficient location tracking, and/or based on other factors. Regardless, in response to a determination to enable efficient location tracking, the method 300 advances to block 304 in which the bed 110 produces an interrogation signal to cause a location tag to produce a response signal. In doing so, in the illustrative embodiment, the bed 110 produces a radio frequency signal using multiple antennas (e.g., the antennas 160, 162) on opposite sides of the bed 110, as indicated in block 306. For example, and as indicated in block 308, the bed 110 may produce a radio frequency signal using antennas (e.g., the antennas 160, 162) on opposite sides of the bed 110 along a lateral dimension (e.g., the antennas 160 162 are on the left and right sides of the bed, rather than the front and back ends of the bed) to increase the probability that a location tag mounted on a left or right side of a doorway (e.g., the location tag 130 on the left side of the doorway 120) will receive the interrogation signal.

As indicated in block 310, in the illustrative embodiment, the bed 110 produces, as the interrogation signal, a radio frequency signal that has a linear polarization, rather than a circular polarization. By confining the electromagnetic radiation of the interrogation signal to a plane along the direction of propagation of the radiation, the bed 110 increases the range of the interrogation signal (e.g., as compared to circular polarization) for a given amount of input power (e.g., thereby conserving energy in the battery 206). When the bed 110 is unplugged from a standard AC power outlet, the interrogation signal is emitted by antennas 160, 162 under the control of reader 150 on a regular basis (e.g., every 50 milliseconds, every 250 milliseconds, every second, etc.) at the discretion of the system designer. That is, when the bed is unplugged from AC power, the assumption is that the bed 110 is potentially being moved from one room to another. When the bed 110 is plugged into a standard AC power outlet, the assumption is that the bed 110 is not in transit such that emitting the interrogation signal from antennas 160, 162 is not needed.

Subsequently, as indicated in block 312, the bed 110 may receive a response signal from a location tag 130. In the illustrative embodiment, and as indicated in block 314, the bed 110 may receive a response signal from a passive location tag mounted to a doorway of a room (e.g., the location tag 130). In block 316, the bed 110 determines the subsequent course of action based on whether a response signal was received. If a response signal was not received, the method 300 loops back to block 304, in which the bed 110 again produces an interrogation signal (e.g., after a predefined time period, such as half a second). Otherwise (e.g., if a response signal was received), the method 300 advances to block 318 of FIG. 4, in which the bed 110 determines, as a function of room data in the response signal, a present location of the bed 110.

Figure 4:
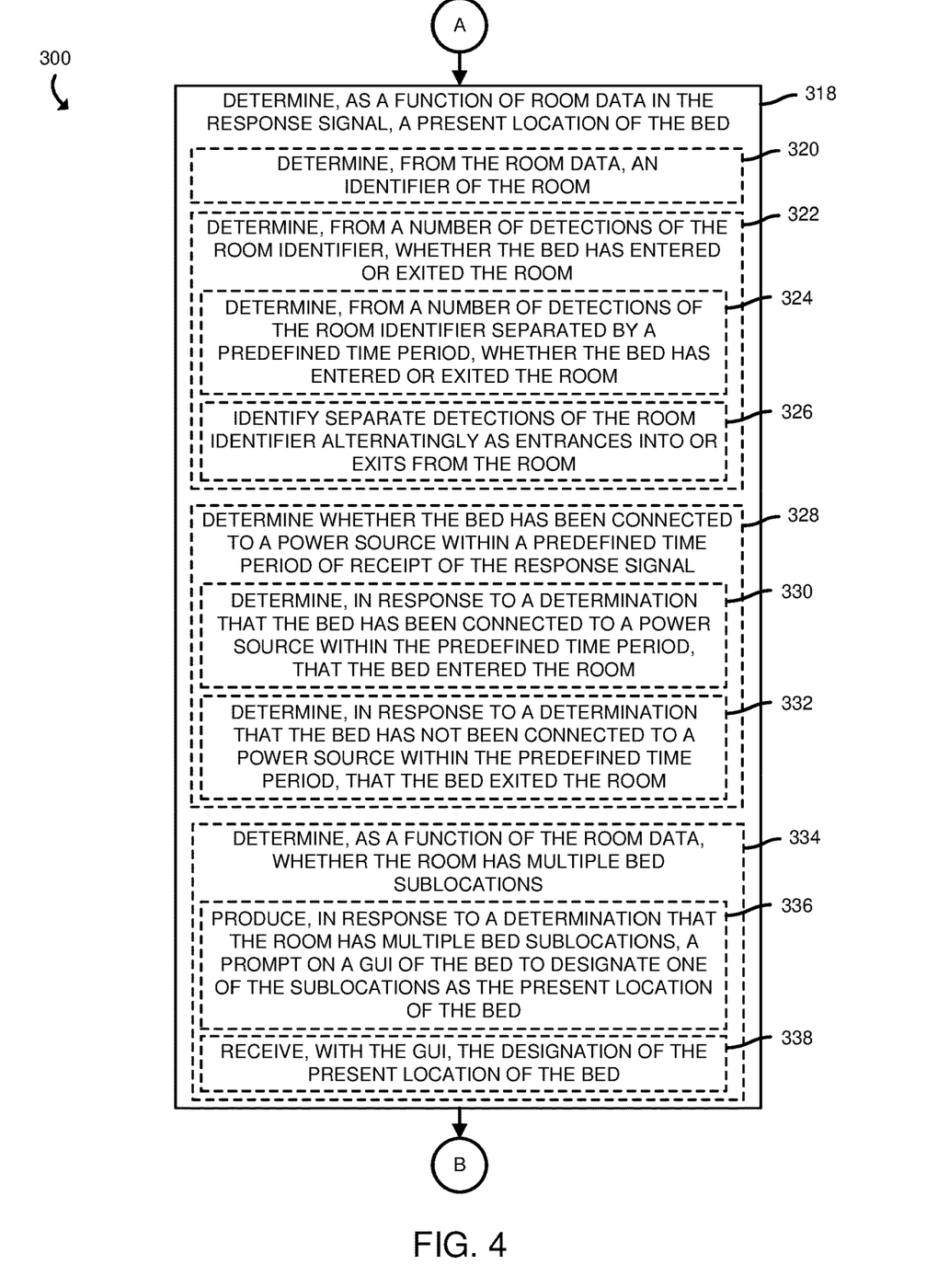

Referring now to FIG. 4, in determining a present location, the bed 110, in the illustrative embodiment, determines, from the room data, an identifier of the room (e.g., a room number), as indicated in block 320. As indicated in block 322, the bed 110 may determine from a number of detections of the room identifier over time, whether the bed has entered or exited the room. In doing so, the bed 110 may determine whether the bed has entered or exited the room based on the number of detections of the room identifier separated by a predefined time period (e.g., separated by at least 10 seconds, to exclude multiple detections of the room identifier as the bed entered the room or exited the room), as indicated in block 324. As indicated in block 326, the bed 110 may identify separate detections of the room identifier alternatingly as entrances into or exits from the room (e.g., the first detection indicates that the bed 110 entered the room, the second detection indicates that the bed 110 exited the room, the third detection indicates that the bed 110 entered the room, etc.).

As indicated in block 328, in determining the location of the bed 110, the bed 110 may determine whether it has been connected to a power source (e.g., a wall outlet) within a predefined time period (e.g., five minutes) of receipt of the response signal from a location tag (e.g., the location tag 130). In doing so, and as indicated in block 330, the bed 110 may determine, in response to a determination that the bed has been connected to a power source within the predefined time period, that the bed 110 entered the room (e.g., the room 140). Conversely, and as indicated in block 332, the bed may determine, in response to a determination that the bed has not been connected to a power source within the predefined time period, that the bed exited the room (e.g., the room 140).

In some embodiments, the bed 110 may determine, as a function of the room data (e.g., in the response signal) whether the room has multiple bed sublocations, as indicated in block 334. For example, the room data may include identifiers of sublocations (e.g., the sublocations 142, 144) where the bed 110 may be positioned within the room. As such, and as indicated in block 336, the bed 110 may produce, in response to a determination that the room has multiple bed sublocations, a prompt on a graphical user interface (e.g., the graphical user interface 202) for a user (e.g., a caregiver moving the bed 110) to designate one of the sublocations as the present location of the bed 110. In block 338, the bed 110 may receive, with the graphical user interface 202 (e.g., by the caregiver selecting the sublocation from a list) a designation of the present location (e.g., one of the bed sublocations 142, 144) of the bed 110 within the room (e.g., the room 140). Subsequently, the method 300 advances to block 340 of FIG. 5, in which the bed 110 may send, to a remote computer device (e.g., the remote computer device(s) 220), data indicative of the present location of the bed 110.

Figure 5:
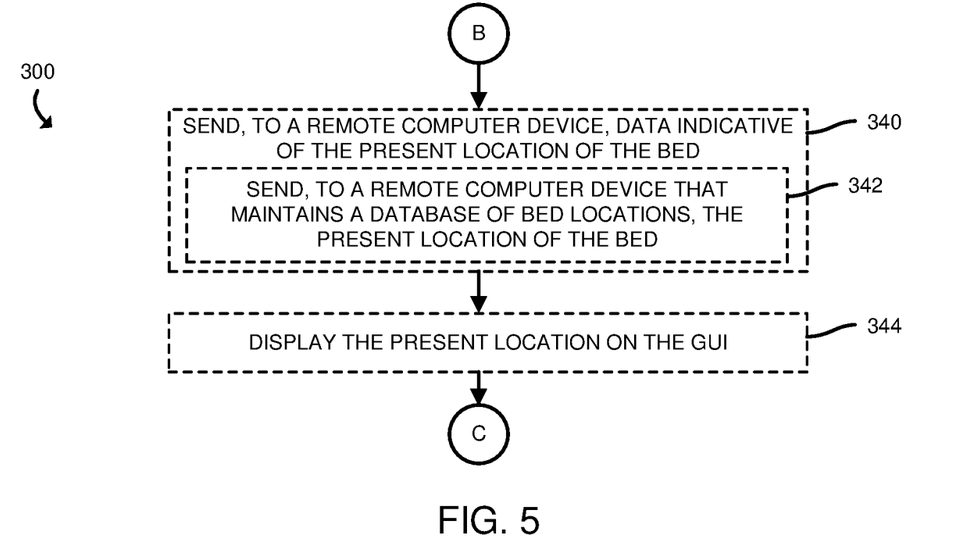

Referring now to FIG. 5, as indicated in block 342, in sending the data indicative of the present location of the bed 110, the bed 110 may send the data to a remote computer device that maintains a database of bed locations (e.g., the remote computer device(s) 220 may operate an EMR system that tracks the locations of medical equipment, such as the bed 110). Additionally or alternatively, and as indicated in block 344, the bed 110 may display the present location of the bed 110 on the graphical user interface 202. Subsequently, the method 300 loops back to block 302 in which the bed 110 again produces an interrogation signal. While the method 300 has been described above as being performed by a bed, it should be understood that in other embodiments, the method 300 may be performed by another medical device (e.g., a wheelchair) equipped with the tag reader 150, antennas 160, 162 and other components similar to those described with reference to FIG. 2.

While certain illustrative embodiments have been described in detail in the drawings and the foregoing description, such an illustration and description is to be considered as exemplary and not restrictive in character, it being understood that only illustrative embodiments have been shown and described and that all changes and modifications that come within the spirit of the disclosure are desired to be protected. There exist a plurality of advantages of the present disclosure arising from the various features of the apparatus, systems, and methods described herein. It will be noted that alternative embodiments of the apparatus, systems, and methods of the present disclosure may not

The invention claimed is:

1. A patient bed comprising:
a tag reader connected to antennas on opposite sides of the patient bed; and
circuitry configured to:
produce, with the tag reader and the antennas, an interrogation signal from the opposite sides of the patient bed, to cause a location tag mounted to a doorway of a room to produce a response signal;
receive, with the tag reader and with one of the antennas, the response signal from the location tag; and
determine, as a function of room data in the response signal, a present location of the patient bed including determining, from a number of detections of a room identifier by the patient bed, whether the patient bed has entered or exited the room.

2. The patient bed of claim 1, wherein to produce the interrogation signal comprises to produce a radio frequency signal having a linear polarization.

3. The patient bed of claim 1, wherein to determine, as a function of the room data, a present location of the patient bed comprises to determine, from the room data, an identifier of the room.

4. The patient bed of claim 1, wherein the circuitry is further configured to display, on a graphical user interface, data indicative of the present location of the patient bed.

5. The patient bed of claim 1, wherein to determine, from a number of detections of the room identifier, whether the patient bed has entered or exited the room comprises to determine, from a number of detections of the room identifier separated by a predefined time period, whether the patient bed has entered or exited the room.

6. The patient bed of claim 1, wherein the circuitry is further configured to identify separate detections of the room identifier alternatingly as entrances into or exits from the room.

7. The patient bed of claim 1, wherein the circuitry is further configured to send, to a remote computer device, data indicative of the present location of the patient bed.

8. A patient bed comprising:
a tag reader connected to antennas on opposite sides of the patient bed; and
circuitry configured to:
produce, with the tag reader and the antennas, an interrogation signal from the opposite sides of the patient bed, to cause a location tag mounted to a doorway of a room to produce a response signal;
receive, with the tag reader and with one of the antennas, the response signal from the location tag; and
determine, as a function of room data in the response signal and further as a function of whether the patient bed has been connected to a power source within a predefined time period of receipt of the response signal, a present location of the patient bed.

9. The patient bed of claim 8, wherein the circuitry is further configured to determine, in response to a determination that the patient bed has not been connected to a power source within the predefined time period, that the patient bed exited the room.

10. The patient bed of claim 8, wherein the circuitry is further configured to determine, in response to a determination that the patient bed has been connected to a power source within the predefined time period, that the patient bed entered the room.

11. A patient bed comprising:
a tag reader connected to antennas on opposite sides of the patient bed; and
circuitry configured to:
produce, with the tag reader and the antennas, an interrogation signal from the opposite sides of the patient bed, to cause a location tag mounted to a doorway of a room to produce a response signal;
receive, with the tag reader and with one of the antennas, the response signal from the location tag;
determine, as a function of room data in the response signal, a present location of the patient bed;
determine, as a function of the room data, whether the room has multiple patient bed sublocations;
produce, in response to a determination that the room has multiple sublocations, a prompt on a user interface of the patient bed, to designate one of the sublocations as the present location of the patient bed; and
receive, with the user interface, the designation of one of the sublocations as the present location of the patient bed.

12. A method comprising:
producing, with a tag reader connected to antennas on opposite sides of a patient bed, an interrogation signal from the opposite sides of the patient bed, to cause a location tag mounted to a doorway of a room to produce a response signal;
receiving, with the tag reader and with one of the antennas, the response signal from the location tag; and
determining, by the patient bed and as a function of room data in the response signal, and further as a function of whether the patient bed has been connected to a power source within a predefined time period of receipt of the response signal, a present location of the patient bed.

13. A method comprising:
producing, with a tag reader connected to antennas on opposite sides of a patient bed, an interrogation signal from the opposite sides of the patient bed, to cause a location tag mounted to a doorway of a room to produce a response signal;
receiving, with the tag reader and with one of the antennas, the response signal from the location tag; and
determining, by the patient bed and as a function of room data in the response signal, a present location of the patient bed including determining, from a number of detections of a room identifier by the patient bed, whether the patient bed has entered or exited the room.

14. The method of claim 13, further comprising identifying separate detections of the room identifier alternatingly as entrances into or exits from the room.

15. The method of claim 13, wherein producing the interrogation signal comprises producing a radio frequency signal having a linear polarization.

16. The method of claim 13, wherein determining, as a function of the room data, a present location of the patient bed comprises determining, from the room data, an identifier of the room.

17. One or more computer-readable storage media comprising a plurality of instructions that, when executed, cause circuitry in a patient bed to:
produce, with a tag reader connected to antennas on opposite sides of the patient bed, an interrogation signal from the opposite sides of the patient bed, to cause a location tag mounted to a doorway of a room to produce a response signal;

receive, with the tag reader and with one of the antennas, the response signal from the location tag; and determine, as a function of room data in the response signal, a present location of the patient bed including determining, from a number of detections of a room identifier by the circuitry in the patient bed, whether the patient bed has entered or exited the room.

* * * * *